United States Patent [19]
Fendrock

[11] Patent Number: 5,305,746
[45] Date of Patent: Apr. 26, 1994

[54] DISPOSABLE, PRE-GELLED, SELF-PREPPING ELECTRODE

[75] Inventor: Charles Fendrock, Sudbury, Mass.

[73] Assignee: Aspect Medical Systems, Inc., Framingham, Mass.

[21] Appl. No.: 952,970

[22] Filed: Sep. 29, 1992

[51] Int. Cl.$^5$ ............................................. A61B 5/0402
[52] U.S. Cl. ...................................... 128/641; 128/640
[58] Field of Search ............................. 128/635–641, 128/644, 803; 607/153

[56] References Cited

U.S. PATENT DOCUMENTS

| | | | |
|---|---|---|---|
| 2,887,112 | 5/1959 | Smith | 128/644 |
| 3,490,439 | 1/1970 | Rolston | 128/2.1 |
| 3,774,592 | 11/1973 | Lahr | 128/2.1 E |
| 3,805,769 | 4/1974 | Sessions | 128/2.06 E |
| 3,828,766 | 8/1974 | Krasnow | 128/2.1 E |
| 4,004,578 | 1/1977 | Palmius | 128/640 |
| 4,027,664 | 6/1977 | Heavner, Jr. et al. | 128/2.06 E |
| 4,029,086 | 6/1977 | Corasanti | 128/2.06 E |
| 4,072,145 | 2/1978 | Silva | 128/2.1 E |
| 4,126,126 | 11/1978 | Bare et al. | 128/639 |
| 4,274,419 | 6/1981 | Tam et al. | 128/639 |
| 4,311,152 | 1/1982 | Modes et al. | 128/641 |
| 4,595,013 | 6/1986 | Jones et al. | 128/644 |
| 4,638,807 | 1/1987 | Ryder | 128/644 |
| 4,640,289 | 2/1987 | Craighead | 128/639 |
| 4,640,290 | 2/1987 | Sherwin | 128/642 |
| 4,683,892 | 8/1987 | Johansson et al. | 128/639 |
| 4,706,679 | 11/1987 | Schmidt et al. | 128/639 |
| 4,709,702 | 12/1987 | Sherwin | 128/644 |
| 4,770,180 | 9/1988 | Schmidt et al. | 128/644 |
| 4,928,696 | 5/1990 | Henderson et al. | 128/644 |
| 4,936,306 | 6/1990 | Doty | 128/642 |
| 4,945,911 | 8/1990 | Coben et al. | 128/640 |
| 4,967,038 | 10/1990 | Gevins et al. | 128/644 |
| 4,995,392 | 2/1991 | Sherwin et al. | 128/639 |
| 5,211,174 | 5/1993 | Imran | 128/639 |

Primary Examiner—Lee S. Cohen
Attorney, Agent, or Firm—Hale and Dorr

[57] ABSTRACT

Disclosed is a disposable self-prepping electrode which utilizes an array or mat of flexile tines which serve to part the high impedance outer layers of skin to expose the low impedance, blood enriched layers without scratching or abrading. The tines are preferably imbedded in a conductive gel layer. In an alternate embodiment, a self prepping layer of flexile tines embedded in gel may be a single disposable self-prepping layer that is mounted over a permanent electrode.

19 Claims, 3 Drawing Sheets

DISPOSABLE, PRE-GELLED, SELF-PREPPING ELECTRODE

BACKGROUND OF THE INVENTION

This invention relates to an electrode for use in monitoring electrical body signals and more particularly to a disposable, pre-gelled, self-prepping electrode.

Disposable electrodes applied to the skin are used extensively in the monitoring of electrical activity of body functions. The most widely used electrodes require that the skin be prepared before applying the electrode in order to get good electrical contact. This is usually accomplished by first wiping the skin with alcohol to remove dirt and oils. The skin is then further prepared by abrading the electrode sites with a grit-impregnated solution on a cotton swab or with some other abrasive means to remove the outer layers of skin which generally cause poor electrical contact. The electrodes are then applied to the prepared sites in contact with blood-enriched skin layers, thereby giving a relatively low electrical contact impedance.

Many of the pre-gelled electrodes that are widely used in medical monitoring of electrical body signals are disposable, pre-gelled electrodes. Examples of such electrodes are shown and described in U.S. Pat. No. 3,805,769 issued to Sessions; U.S. Pat. No. 3,828,766 issued to Krasnow; U.S. Pat. No. 4,029,086 issued to Corasanti; U.S. Pat. No. 4,640,289 issued to Craighead; and U.S. Pat. No. 4,945,911 issued to Cohen. These electrodes, however, all require multiple, separate and time consuming steps of skin preparation, to reduce the contact impedance with the skin before they are applied to the body.

To reduce the number of steps required to prepare the skin, several self-preparing electrodes have been developed. U.S. Pat. No. 4,027,664 issued to Heavner describes an electrode having a cover with an abrasive surface to give the applicator of the electrode a ready means to abrade and prepare the skin before application of the electrode. The abrasive means is discarded after application. U.S. Pat. No. 4,995,392 issued to Sherwin utilizes a removable, non-conductive brush through the center of a reusable electrode to perform the skin preparation. U.S. Pat. No. 3,774,592 issued to Lahr utilizes an electrode with an absorbent pad placed against the skin through which a separate stiff-bristled brush is dabbed to micropuncture the skin to prepare it.

Each of the techniques described above also require multiple, separate components or steps to perform the skin preparation even though they are "self-preparing". In many situations in patient monitoring, keeping physical track of multiple, separate components is inconvenient because of the clutter or haste typical, for example, of an operating room or intensive care unit. Requiring separate steps to perform skin preparation makes it difficult to improve contact impedance once the electrode has been applied to the patient or after a medical procedure is underway. If the preparation was inadequate, once the electrode has been applied it must be removed, the skin reabraded, and most likely a new electrode would have to be reapplied, adding additional expense to the additional preparation time. Too much abrasion can cause a skin injury or bleeding, leaving the patient with a lasting wound. Also, when an abrading means incorporated as part of an electrode cover or another separate mechanical abrader is used, it is likely that the results will be varied from patient to patient since the results are dependent upon the type of skin of the patient and the abrading technique used by the person applying the electrode.

U.S. Pat. No. 4,274,419 issued to Tam utilizes a separate hand-held mechanical rotating apparatus to rotate a center abrasive disk which is part of an electrode that spins against the skin and continuously measures skin contact impedance. This technique may give more consistent impedance results, but the need for a rotating apparatus (or separate brushes as described above) to perform skin preparation is also a recurring expense in the case of the brushes which generally cannot be reused, and a very high one-time expense in the case of the rotating apparatus. Such a mechanical abrading device is also prone to cause abrasion skin injuries.

U.S. Pat. No. 4,706,679 issued to Schmidt utilizes a metallic brush similar in function to the one used in U.S. Pat. No. 4,995,392 but that remains in contact with the patient during use. Metal in direct contact with the patient's skin causes chemical half-cell reactions that generate offset voltages at the points of contact, interfering with the sensitive measurement of the low signal voltages of the body.

The application of several electrodes, which is typical for medical monitoring, is very time consuming using known methods because of the steps required and the uncertainty of the skin preparation results. Also, all of the known preparation devices, because of the need to physically handle the multiple, separate items required to prepare the skin, cause risk to the applicator by potential contact with blood and by possible disease transmittal during preparation.

It is therefore a principal object of the present invention to provide a self-prepping electrode which easily and reliably prepares the skin to assume a relatively low electrical contact impedance.

Another object of the present invention is to provide a self-prepping electrode which can prepare the skin without requiring the use of more than one component to be handled by the person applying the electrode.

A still further object of the present invention is to provide a self-prepping electrode which minimizes the chances of the occurrence of any skin abrasion injuries.

SUMMARY OF THE INVENTION

The electrode construction of the self-prepping electrode of the present invention is generally a flexible adhesive pad or carrier with a center electrode having a post or stud to make an electrical connection. On the side of the electrode opposite the post or stud is an electrical pad that contacts a conductive gel layer. Imbedded in the conductive gel layer is a conformable array or mat of flexile tines imbedded in the conductive gel of the electrode. The flexile tines extend beyond the outer surface of the gel to contact the skin as part of the normal application of the electrode to the skin. When pressure is applied to the electrode, the flexile tines are pushed against the skin, which causes the tines to part the high impedance outer layers of skin to expose the low impedance, blood-enriched layers without scratching or abrading. If the impedance is too high, it can be corrected immediately by simply pushing on the electrode with some lateral motion to further penetrate the outer skin layers. The electrode need not be removed. Over-prepping is difficult because the gel between the tines acts as a cushion to prevent injury.

The array or mat of flexile tines is made of a non-metallic material such as plastic. This makes the self-prepping electrode a very inexpensive device to prepare the skin, and this low cost is essential for a disposable electrode. This novel prepping means can be retrofitted to existing, commercially available disposable, semi-disposable, or reusable electrodes to vastly improve their utility at an insignificant cost. Also, the non-metallic material eliminates the possibility of offset voltages being created by metallic skin contact.

As a convenience to the person applying the electrode, a peel-away alcohol pad is provided to wipe the skin before applying the electrode.

Since the means of preparation is entirely contained in the underside of the electrode, the possibility of contact with patient blood by the person applying the electrode is virtually eliminated.

These and other feature and objects of the present invention will be more fully understood from the following detailed description which should be read in light of the accompanying drawings in which corresponding reference numerals refer to corresponding parts throughout the several view.

DETAILED DESCRIPTION OF THE PREFERRED EMBODIMENT

Figure 1:
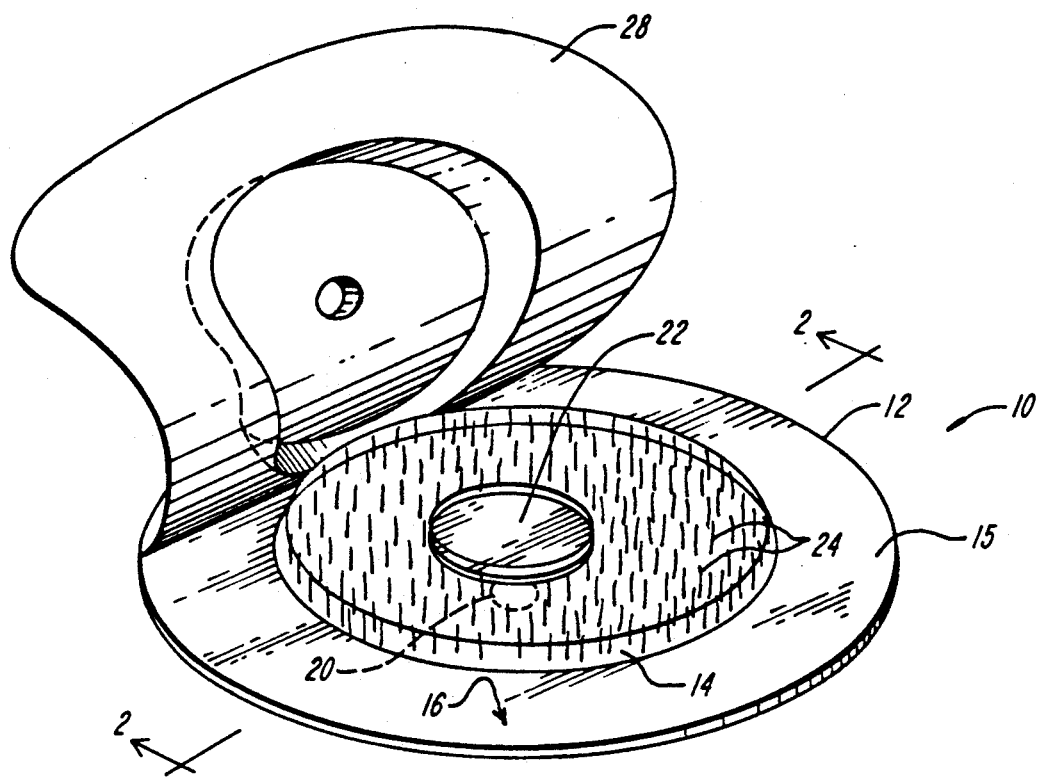
FIG. 1 is a perspective view of the self-prepping electrode of the present invention.
Figure 2:
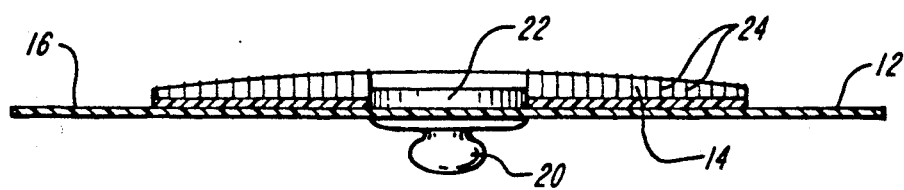
FIG. 2 is a cross-sectional view of the self-prepping electrode shown in FIG. 1 taken along lines 2—2 of FIG. 1.
Figure 3:
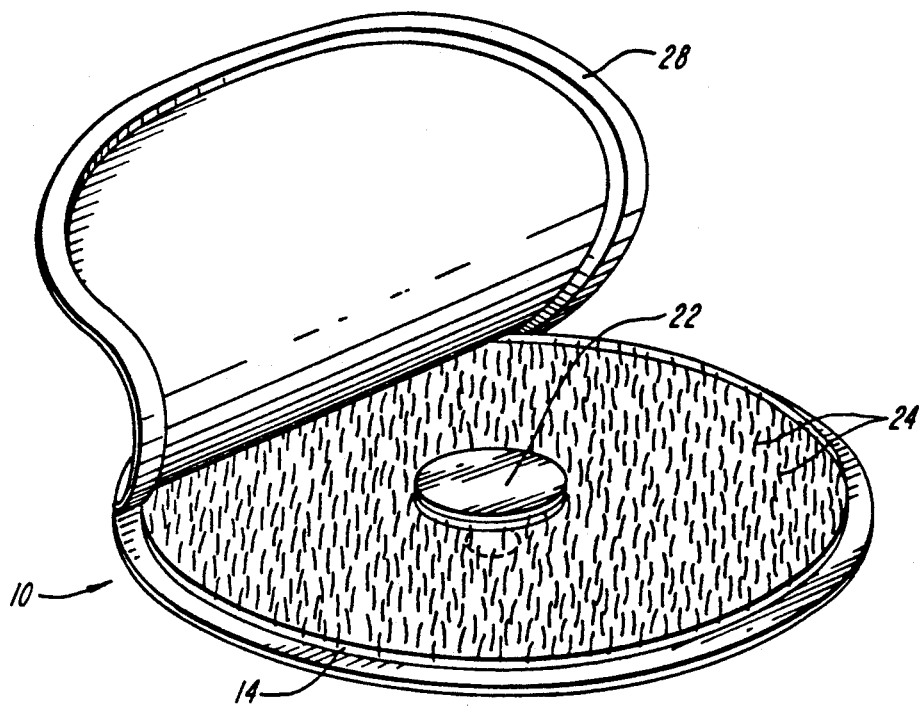
FIG. 3 is a perspective view of an alternate embodiment the self-prepping electrode of the present invention.

The present invention is a novel self-prepping electrode for monitoring the electrical activity of body functions. Referring to FIGS. 1 and 2, one implementation of the self-prepping electrode 10 of the present invention includes a flexible tape 12 or other similar material with adhesive 15 on the side 16 of the tape designed to contact the skin. A layer of conductive gel 14 is placed over the adhesive. The gel may be any of the commercially available gels which may be obtained from a large number of suppliers including Promeon of Minneapolis, Minn. In the preferred embodiment the layer of gel has a thickness between 0.020 to 0.100 inches, although the layer of gel can certainly be thinner or thicker depending on how the electrode is to be used (e.g. thicker if the electrode will be in place on the patient for a considerable period of time). In other embodiments, such as the embodiment shown in FIG. 3, the electrode 10 does not include the adhesive annulus shown in FIG. 1, but instead includes a flexible carrier 18 with gel 14 that is both conductive and adhesive which will enable the electrode to adhere to the body.

A center electrode stud 20 such as the commonly used "pajama snap," is incorporated in the rear of the electrode 10 to make an electrical connection to the monitoring apparatus. Alternately, a pre-attached wire could be used in place of the stud connection. An electrical pad 22 such as the commonly used silver/silver chloride "button" or "pellet" contacts the gel 14 and creates a very low offset voltage. Such pads are constructed of materials commonly used in the industry and available from suppliers, such as Tolas Health Care Packaging of Feasterville, Pa. and Graphic Controls of Buffalo, N.Y.

Imbedded in the gel 14 is a conformable array or open "mat" of short, non-conductive, flexile tines 24 which serve to separate and penetrate through, but not scratch or abrade, the high impedance outer layers of skin down to the low impedance, blood-rich layers which will then come in electrical contact with the center electrode. The tines are preferably between 0.025 inches and 0.110 inches long and between 0.002 and 0.015 inches thick. The length and width of the tines as well as the ratio of the length to width of the tines depend on a number of factors including the type of material out of which the tines are made, the desired flex of the tines, and the material (i.e. gel) in which the tines are embedded.

The flexile tines 24 can be simply made, for example, by clipping the "hook" ends off a Velcro material, leaving a mat of short, still flexile tines that can be cut to the desired height and shape. An array or mat of flexible tines 24 can also be specially fabricated for this specific application through injection molding or some other commonly used method. A protective cover 28 is placed over the gel 14 or adhesive 15 to prevent the adhesive from drying out to prevent the and introduction of contaminants during storage. This cover 28 is discarded before use.

Figure 4:
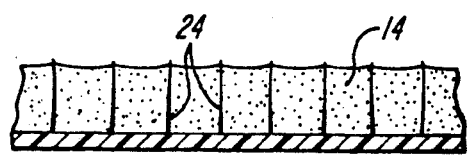
FIG. 4 is a close-up cross-sectional view of the flexile tines of the present invention imbedded in a conductive gel of the self-prepping electrode shown in FIG. 1.
Figure 5:
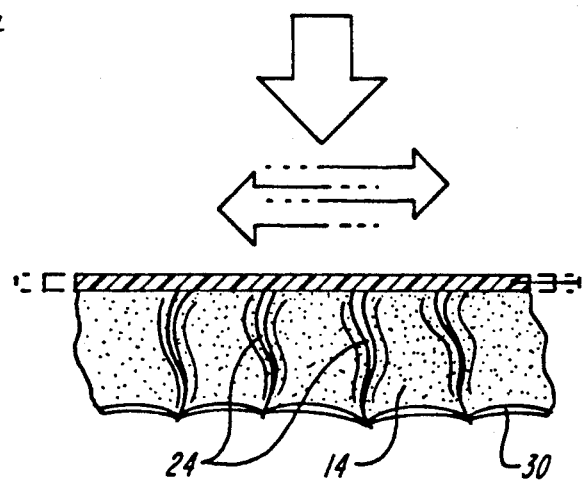
FIG. 5 is a close-up cross-sectional view of the movement of the flexile tines imbedded in the conductive gel of the self-prepping electrode shown in FIG. 1.

Referring to FIGS. 4 and 5, the electrode 10 is forced toward the skin of the patient when being applied and the electrode 10 may also be moved side to side to enable the tines 24 to penetrate the outer skin layers 30. The conductive and possibly adhesive gel 14, that fills the voids between the flexile tines 24, provides electrical contact between the center electrode 22 and the skin as it squeezes into the small perforations in the skin surface 30 made by the flexile tines 24 thereby providing the low impedance electrical contact. The gel 14 provides a cushion against which the skin 30 is pushed as the electrode is applied to reduce the possibility of skin injury and to provide comfort during patient wear.

Figure 6:
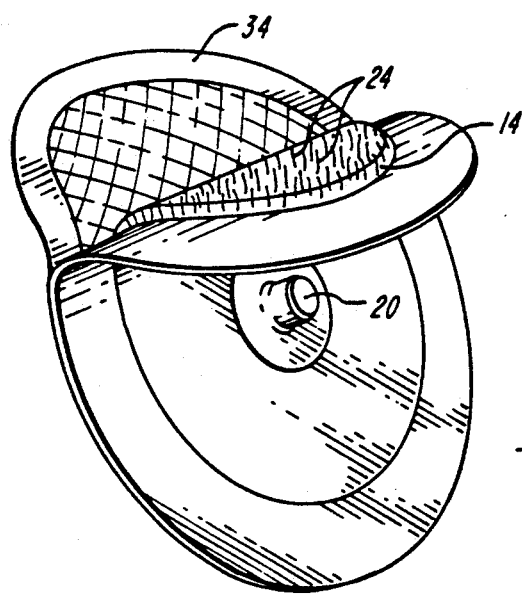
FIG. 6 is a perspective view of the self-prepping electrode of the present application showing a protective cover which protects the adhesive layer of the self-prepping electrode shown in FIG. 1.

Referring to FIG. 6, an alternative embodiment of the electrode of the present invention includes an integral, peel-away, disposable alcohol wipe pad 34 attached to the electrode 10 that the person applying the electrode uses to wipe away dirt and oil on the skin at the electrode site before applying the electrode.

Figure 7:
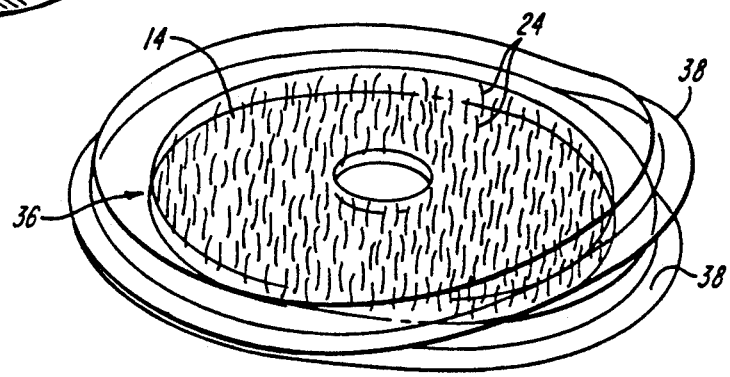
FIG. 7 is a perspective view of an alternate embodiment of the self-prepping electrode shown in FIG. 1 wherein a layer flexile tines embedded in conductive gel is implemented as a disposable component of an otherwise reusable electrode.

Another alternate embodiment of the electrode of the present invention is shown in FIG. 7. This electrode includes an array or mat 36 of flexile tines that is designed as a disposable part of an otherwise reusable electrode. The mat or array 36 of flexile tines 24 is embedded in conductive gel 14 sandwiched between two peel-away layers 38, with one side being applied to the reusable electrode, and the other side being applied to the patient. After use, the flexile tine assembly imbedded in the gel is removed from the reusable portion of the electrode and is discarded.

Figure 8:
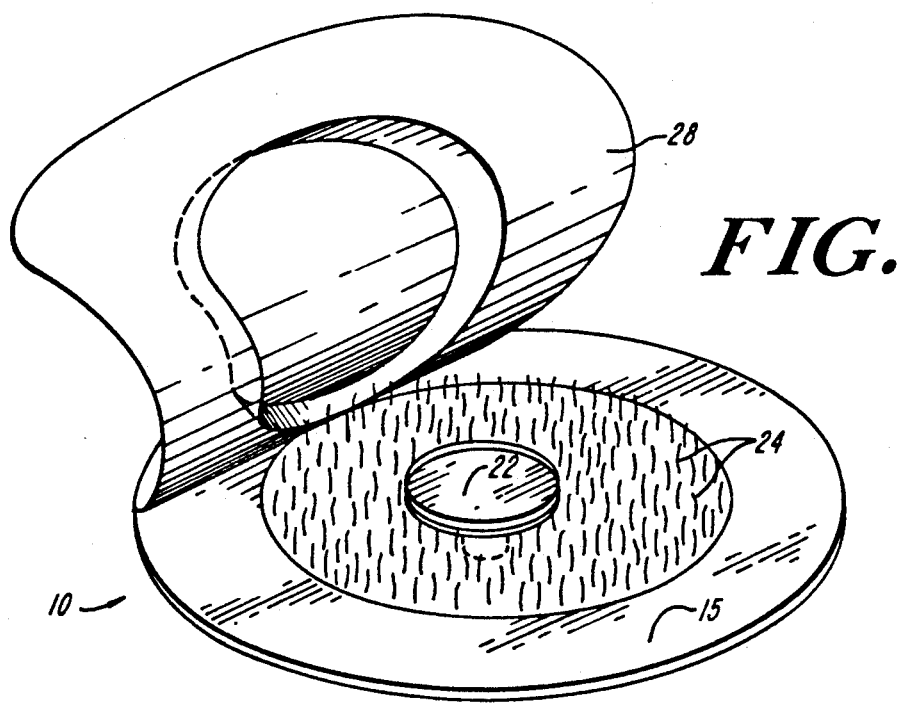
FIG. 8 is a perspective view of an alternate embodiment of the self-prepping electrode shown in FIG. 1 wherein the tines surround an electrical pad without being embedded in gel.

In an alternate embodiment, imbedded in the gel is an annular ring of short, non-conductive, flexile tines 24 on a solid carrier with a center opening to permit electrical contact with the center electrode. In another alternate embodiment shown in FIG. 8 the electrode 10 utilizes flexile tines 24 that are "dry", i.e., are manufactured without gel. This embodiment would use a commercially available electrolyte creme, such as Redux from Hewlett Packard, Palo Alto, Calif., that is applied to the flexile tine and electrical pad areas just prior to application to the patient.

The electrode of the present invention provides a single, integrated means to prepare the skin with the application of the electrode. It eliminates the need for separate abrasive parts, brushes, grit-impregnated solutions and applicators. Application of the electrode and achieving a very low contact impedance nearly instantly after application is virtually guaranteed. The electrode described is capable of achieving excellent electrical contact, 5,000 Ohms or less with the living tissue underlying the electrode. Because impedance can be measured without removing the electrode from the skin surface, repeatable results may be achieved and contact resistance can be improved without removing the electrode and without creating offset voltages that can interfere with the measurement. This adjustment can be performed quickly at low cost with little risk of causing skin injury and with minimal risk of exposing the person applying the electrode to the patients blood and possible disease.

While the foregoing invention has been described with reference to its preferred embodiments, various alterations and modifications will occur to those skilled in the art. All such alterations and modifications are intended to fall within the scope of the appended claims.

I claim:

1. An electrode for monitoring electrical signals of a body comprising:
   an electrical pad;
   means for parting and keeping parted outer layers of skin on the body without removing any skin, said means for parting being non-conductive and being arranged in close proximity to said electrical pad.

2. The electrode of claim 1 wherein said means for parting is embedded in, and extends from a surface of, a layer of conductive gel mounted on one surface of an electrical pad.

3. The electrode of claim 2 wherein said means for parting is an array of flexible non-conductive tines extending from said surface of said layer of conductive gel.

4. The electrode of claim 3 wherein said flexible tines are substantially parallel to each other.

5. The electrode of claim 3 wherein said flexible tines are of substantially uniform height.

6. The electrode of claim 2 wherein said layer of conductive gel is between 0.025 and 0.110 inches thick.

7. The electrode of claim 2 further comprising a flexible base and an adhesive layer arranged on a side of the electrode intended to contact the body between said flexible base and said layer of conductive gel.

8. The electrode of claim 7 further comprising an adhesive layer positioned over a side of said layer of gel designed to contact the body.

9. The electrode of claim 1 wherein said means for parting comprises an array of flexible non-conductive tines.

10. The electrode of claim 9 wherein said flexible tines are of substantially uniform height.

11. The electrode of claim 9 wherein said flexible tines are between 0.025 and 0.110 inches high.

12. The electrode of claim 9 wherein said flexible tines are between 0.002 and 0.015 inches thick.

13. The electrode of claim 9 wherein said flexible tines are substantially parallel to each other.

14. The electrode of claim 1 further comprising a flexible base and an adhesive layer arranged on a side of the electrode intended to contact the body between said flexible base and said means for parting.

15. The electrode of claim 14 wherein said adhesive layer is arranged around said means for parting.

16. A removable self-prepping layer for use with a monitoring electrode comprising:
   a layer of conductive gel;
   an array of flexible tines arranged in said layer of gel so that said tines extend beyond a surface of said gel.

17. The removable self-prepping layer of claim 16 further comprising at least one layer of adhesive mounted over at least one surface of said layer of conductive gel.

18. The removable self-prepping layer of claim 17 wherein a layer of adhesive is placed over top and bottom surfaces of said layer of conductive gel.

19. The removable self-prepping layer of claim 16 wherein said tines extend beyond only one surface of said gel.

* * * * *